Figure 1:
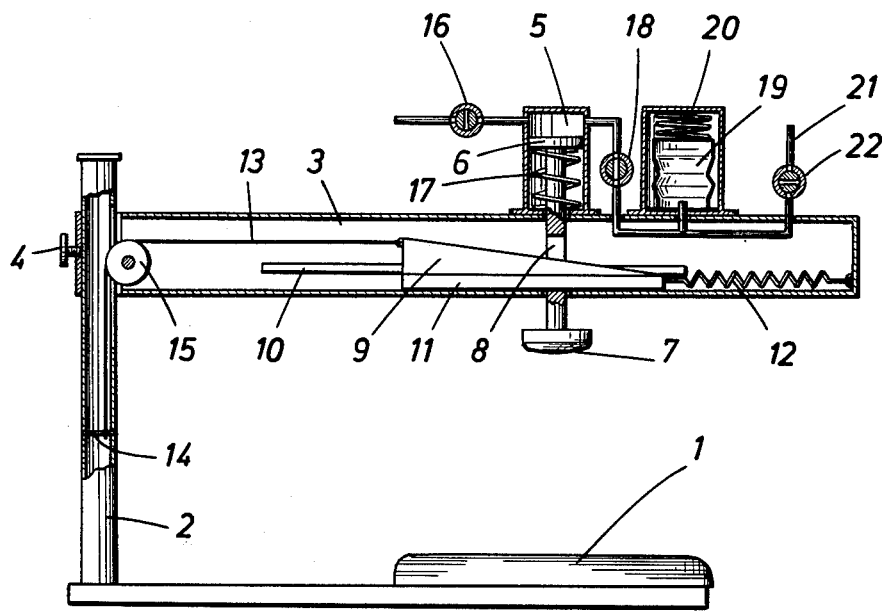

United States Patent [19]

Ragailler

[11] 3,965,893
[45] June 29, 1976

[54] ARTIFICIAL RESPIRATION APPLIANCE

[76] Inventor: Franz Ragailler, Schmiegstrasse 6, Eferding, Austria

[22] Filed: May 21, 1975

[21] Appl. No.: 579,670

[52] U.S. Cl. .............................. 128/145.8; 128/28
[51] Int. Cl.² ........................................ A61M 16/00
[58] Field of Search ........... 128/145.5, 145.6, 145.7, 128/145.8, 30.2, 28, 30

[56] References Cited
UNITED STATES PATENTS

| | | | |
|---|---|---|---|
| 3,254,645 | 6/1966 | Rand et al. | 128/28 |
| 3,336,920 | 8/1967 | Thomas | 128/145.8 |
| 3,348,536 | 10/1967 | Tambascia | 128/145.8 |
| 3,351,092 | 11/1967 | Ingerfield et al. | 128/145.8 |
| 3,509,899 | 5/1970 | Hewson | 128/145.5 |

Primary Examiner—Robert W. Michell
Assistant Examiner—Henry J. Recla
Attorney, Agent, or Firm—Kurt Kelman

[57] ABSTRACT

The appliance serves to subject a human patient to artificial respiration. A cushion is adapted to be disposed under the back of the patient. A piston-cylinder actuator is carried by a fixed support. An inlet valve is connected between a source of an inhalable gas under superatmospheric pressure and said actuator and is adapted to admit inhalable gas from said source to said actuator on one side of said piston. An outlet valve is connected between said actuator and a reservoir which is adapted to expand in response to its internal pressure. Said outlet valve is adapted to release inhalable gas from said actuator on said one side of said piston into said reservoir. A conduit which incorporates a shut-off valve connects said reservoir to said respiration mask. First spring means oppose a movement of said piston under the influence of said inhalable gas admitted to said actuator from said source. Second spring means oppose the expansion of said reservoir. A ram is mounted to be adjustable relative to said support into engagement with the chest of said patient and is connected to said piston to be forced against the chest of said patient by the movement of said piston under the influence of said inhalable gas admitted to said piston from said source. A stop is arranged to limit the movement of said piston under the influence of said inhalable gas admitted to said actuator from said source. An adjusting mechanism is arranged to positively adjust said stop in response to the adjustment of said ram relative to said support into engagement with said chest, whereby said stop is moved to a position in which said stop limits said movement of said piston to an extent that depends on the diameter of said chest.

7 Claims, 2 Drawing Figures

ARTIFICIAL RESPIRATION APPLIANCE

This invention relates to an appliance for subjecting a human being to artificial respiration, comprising a cushion adapted to be disposed under the patient and a ram which is adapted to be engaged with the chest of the patient and to be forced against the chest by means of a piston-cylinder actuator comprising a piston which is movable against spring force by pressure applied by an inhalable gas which is under superatmospheric pressure and admitted and released by controlled inlet and outlet valves and which is supplied to the patient through a respiration mask when the piston has performed a predetermined number of cycles and has then been relieved of the pressure of the inhalable gas.

In the use of a known appliance of this kind the patient to be treated lies with his back on the cushion, the ram carried by the actuator is engaged with the patient's chest, and the actuator is connected to the cushion by straps so that the actuator when subjected to fluid pressure is retained by the straps conected to the cushion and can apply pressure to the chest of the patient. The straps by which the actuator is fixed have a plurality of fixing points so that they can be adapted to patients having different body dimensions. The actuator is usually connected to an oxygen bottle, which is also used to supply inhalable gas to the patient. When five piston cycles have been performed to massage the heart, the valves are controlled to interrupt the communication between the oxygen bottle and the actuator and the patient is permitted to inhale oxygen in that the oxygen bottle is connected by a reducing valve to the respiration mask. This repsiration phase is succeeded by a repeated operation of the actuator to massage the heart.

It is desired to select the pressure applied by the piston of the actuator to the patient's chest to the condition of each patient. For this purpose the pressure applied to the piston can be varied within certain limits. Besides, the reducing valve can be controlled by an adjusting switch to control the volume rate at which oxygen is supplied to be inhaled. It is apparent that the known appliance can be adjusted to different requirements of different patients as regards the massage pressure and the volume rate of inhalation. The apparatus has the disadvantage that this adjustment can be performed only by a skilled person who can estimate for each patient the pressure to be applied to the piston and the pressure of the oxygen to be inhaled. Because oxygen is supplied to the patient directly from the oxygen bottle only through an interposed reducing valve, a failure of the reducing valve may involve a risk that oxygen under an excessively high pressure may be supplied to the patient.

It is an object of the invention to provide an appliance for subjecting a human being to artificial respiration, which appliance permits of an automatic adaptation of the massage pressure and of the quantity of inhalable gas supplied to each patient so that a manual adjustment of the appliance is no longer required.

In an appliance of the kind defined first hereinbefore this object is accomplished according to the invention in that a stop is provided which is adapted to limit the stroke of the actuator and which is adapted to be positively adjusted as the ram is applied to the patient's chest, and that the respiration mask is connected by a conduit provided with a shut-off valve to a reservoir, which is adapted to expand against spring force and to receive the inhalable gas as it is expelled from the cylinder of the actuator during each return stroke of the piston. The invention utilizes the fact that the pressure required to massage the heart and the quantity of oxygen to be inhaled depend on the diameter of the patient's chest. The larger the diameter of the chest, the larger may be the piston stroke selected for the massage of the heart and the larger is also the quantity of oxygen to be inhaled. For this reason the invention provides an arrangement in which the stroke of the actuator is positively adjusted by the displacement of a suitable stop as the ram is engaged with the patient's chest. Depending on the adjusted stroke, a larger or smaller quantity of gas is required to apply pressure to the actuator and this quantity of gas is forced into a reservoir during the return stroke so that the reservoir receives a quantity of gas which depends on the diameter of the chest. When the actuator has performed five massage cycles, the reservoir contains gas in a quantity which is in accordance with the size of the patient's chest and which ensures the supply of the proper quantity of inhalable gas during the subsequent respiration phase. The reservoir may be provided by a bellows or by a cylinder and a piston slidable therein, or the like, and gas can enter the reservoir only against spring force, which forces the inhalable gas out of the reservoir so that the pressure under which the inhalable gas is supplied to the patient depends on the adjusted spring force and cannot increase beyond a certain value, which is harmless.

The stop for limiting the stroke might be adjusted by a drive mechanism which is operated as the ram is adjusted. A simpler arrangement will be obtained if, according to the invention, the stop for limiting the stroke of the actuator consists of a wedge which is adjustable transversely to the direction of movement of the piston so that the adjustment of the wedge transverse to the direction of movement of the piston changes that height of the wedge which effectively limits the stroke of the piston. The taper of the wedge permits of an adaptation of the stroke to the elevation of the ram, which elevation depends on the diameter of the chest.

A simple structure will be obtained if, according to the invention, the wedge is mounted on a vertically adjustable arm, the actuator is directly connected to the ram, a rope is connected to the wedge and is secured to a guide for the arm which carries the actuator, and said rope is tensioned by a spring acting on the wedge and is preferably trained around a reversing pulley mounted on the carrying arm. Depending on the direction in which the carrying arm is moved along its guide, the wedge is either pulled by the rope toward the guide against the force of the spring or is pulled away from the guide by the spring. A specific position of the wedge is associated with each elevation of the carrying arm. If the rope is trained around a reversing roller mounted on the carrying arm, the rope will always extend parallel to the guide and to the carrying arm so that the rope can be protected in that it is accommodated in the hollow guide and the hollow carrying arm.

To limit the stroke of the piston, the stop must cooperate with suitable stops associated with the actuator. In this connection the invention provides a simple arrangement in which the wedge extends into a slot formed in the ram of the piston so that the upper edge of the slot forms the cooperating stop.

To provide an appliance which is as compact as possible and has a low overall height, it is a feature of the invention that the actuator is non-adjustable and is connected to the ram by a drive mechanism which comprises two levers which are rotatable about a common horizontal axis and which are adapted to be non-rotatably connected to each other in different angular positions, and the stop for limiting the stroke is adjustable by the lever which is associated with the ram. In this case the adjustment to a chest having a given diameter is accomplished by a pivotal movement of the lever associated with the ram relative to the lever connected to the actuator so that the stop for limiting the stroke is also positively adjusted. This embodiment has the advantage that the actuator, the reservoir for the inhalable gas, and the connecting conduits provided with the suitable valves need not be carried by an adjustable carrying arm but may be accommodated in a stationary housing.

If the adjustment of the stop for limiting the stroke is derived from the lever which is associated with the ram, it will be desirable to connect the stop for limiting the stroke to the lever associated with the ram by means which have a backlash to the extent of the pivotal movement performed by the lever in response to the largest movement of the actuator. This feature will ensure that the stop for limiting the stroke does not follow the stroke to be performed by the ram to massage the heart.

Figure 2:
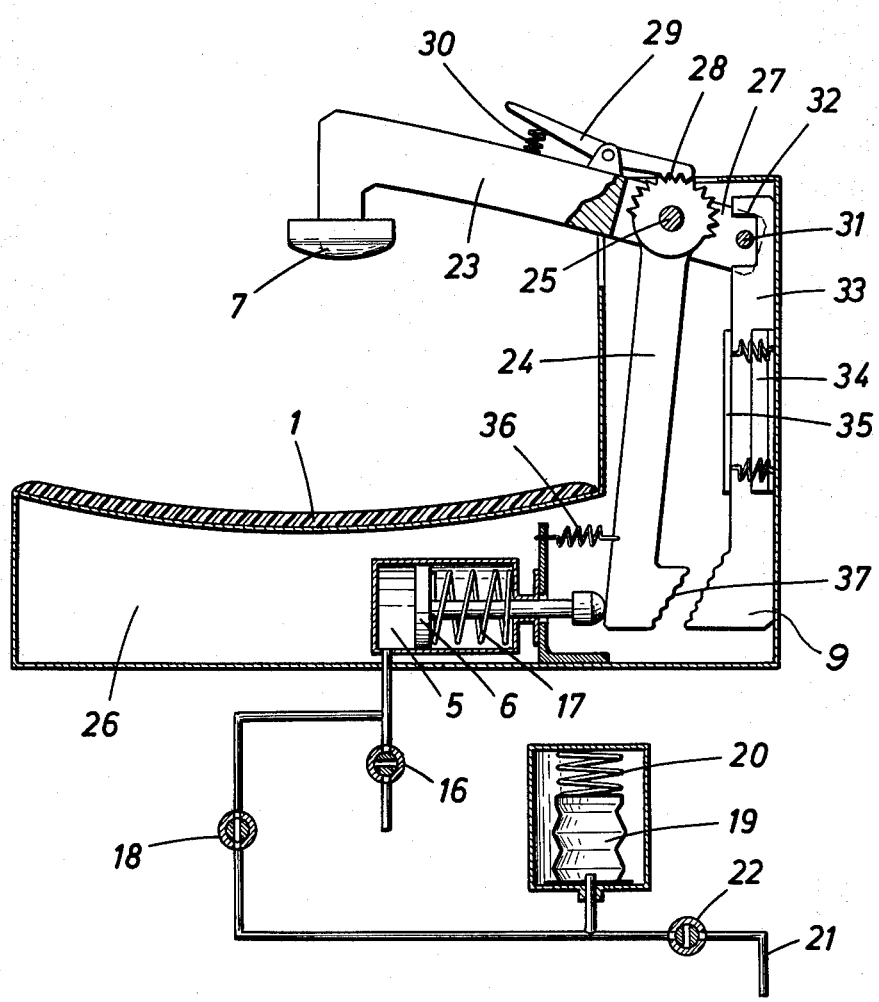

Embodiments of the invention are shown by way of example on the accompanying drawings, in which FIG. 1 is a diagrammatic sectional view showing an appliance for subjecting a human being to artificial respiration and FIG. 2 is a sectional view similar to FIG. 1 and showing another embodiment.

In the embodiment shown in FIG. 1, a tubular guide 2 is connected to a cushion 1 to be placed under a patient. An arm 3 is slidable along said guide 2 and is adapted to be fixed in different positions by a set screw 4. The arm 3 carries a cylinder 5 of an actuator, which comprises a piston 6 that is connected to a ram 7. The ram 7 has a slot 8, which receives a wedge 9, which is mounted in the hollow arm 3 to be movable transversely to the direction of movement of the piston. For this purpose the arm 3 is provided on its inside surface with guide ribs 10, which cooperate with lateral guide projections 11 of the wedge 9. A tension spring 12 connected to the arm 3, and a rope 13 are connected to opposite sides of the wedge 9. The other end of the rope 13 is secured to a pin 14 provided in the guide tube 2. The rope is trained around a guide pulley 15 rotatably mounted in the arm 13. In this arrangement the courses of the rope extending within the guide tube 2 and within the arm 3 are always parallel to the axes of the guide 2 and the arm 3, respectively.

When the set screw 4 has been loosened and the arm 3 is lowered until the ram 7 rests on the chest of the patient, who lies with its back on the cushion 1, the spring 12 will displace the wedge 9 as the arm 3 is lowered because the rope course extending in the arm 3 is increased in length in accordance with the descent. The displaced wedge 9 will limit the stroke because the piston 6 can be lowered only until the upper edge of the slot 8 rests on the upper wedge surface. The lowered arm 3 is then fixed in position by the set screw 4. When the appliance is then started an inlet valve 16 is controlled to admit inhalable gas under superatmospheric pressure, e.g., oxygen, into the cylinder 5, so that pressure is applied to the piston 6 and the same is moved against the force of a return spring 17 and the ram 7 performs a suitable massage stroke. Thereafter the inlet valve 16 is closed and the outlet valve 18 is opened so that the gas contained in the cylinder 5 is forced by the return spring 17 to flow through the outlet valve 18 into a reservoir bellows 19, which expands against the force of a spring 20.

A conduit 21 which incorporates a shut-off valve 22 connects the reservoir 19 to a respiration mask so that when the shut-off valve 22 is open the gas contained in the reservoir 19 is forced by the spring 20 out of the reservoir 19 into the respiration mask. The valves 16, 18, and 22 are controlled in such a manner that the ram 7 performs five cycles, and after the forward stroke of each cycle the gas admitted to the actuator is forced into the reservoir 19. After the fifth cycle of the actuator 5, 6 the shut-off valve 22 is opened and the inhalable gas stored in the reservoir is supplied to the patient. After this respiration phase, the ram 7 is again caused to perform five cycles and the sequence of operations which has been described is repeated.

Because the adaptation of the appliance according to the invention to the diameter of the patient's chest results automatically in a limitation of the stroke of the ram 7 in accordance with the diameter of the chest and this limitation of the stroke determines also the quantity of gas which is supplied, the pressure applied to the patient's chest and the quantity of gas supplied to be inhaled are automatically adjusted for each patient, whether he is a child or adult. The spring 20 acting on the reservoir 19 determines the maximum pressure under which the gas to be inhaled is supplied to the patient so that there is no risk that the gas to be inhaled may be supplied to the patient under the pressure applied to the piston 6.

FIG. 2 shows an artificial respiration appliance which is basically similar to the appliance shown in FIG. 1. The main difference between the two appliances resides in that in the embodiment of FIG. 2 the ram is not directly connected to the piston 6 of the actuator but is connected to said piston by two levers 23 and 24, which are mounted in a housing 26 for rotation on a common horizontal pivot 25. The housing 26 carries the cushion 1. The relative angular position of the levers 23 and 24 is adjustable so that in this embodiment too the ram 7 connected to the lever 23 can be lowered for adjustment to the diameter of the chest. For this purpose the lever 23 is formed with a fork 27 at its end remote from the ram 7 and the lever 24 extends into said fork. The pivot 25 extends through the fork 27 and the lever 24. The lever 24 carries a gear segment 28, which interlocks with a detent lever 29, which is mounted on the lever 23 and is urged to its interlocking position by a spring 30. To adjust the appliance to the diameter of a given chest, it is sufficient to depress the detent lever 29 so as to elminate the non-rotatable connection between the levers 23 and 24 and to impart a pivotal movement to the lever 23 and ram 7 until the latter engages the chest. The detent lever 29 is then released so that the two levers 23 and 24 are automatically interlocked.

During the pivotal movement of the lever 23 the wedge 9 is also correspondingly adjusted because the fork 27 of the lever 23 is extended in length and at its end carries a coupling pin 31, which extends into a corresponding aperture 32 in a rod 33 for adjusting the wedge 9. The wedge 9 and the adjusting rod 33 are guided by a guide 34. The adjusting rod 33 is forced against the guide 34 by a spring-loaded pressure plate 35.

The aperture 32 is dimensioned that the coupling pin 31 does not engage the rod 33 during the maximum stroke of the piston 6 so that the wedge 9 is adjusted only during the adjustment of the appliance to the diameter of a given chest but is not adjusted during the operation of the appliance.

A return tension spring 36 is provided to hold the lever 24 in engagement with the piston rod. The cooperating stop surface 37 of the lever 24 is serrated or provided with a friction facing so that the wedge 9 cannot be displaced when this surface 37 is forced against the wedge surface, which is formed with mating serrations or a similar friction facing.

What is claimed is:

1. An appliance for subjecting a human patient to artificial respiration, which comprises
   a cushion adapted to be disposed under the back of the patient,
   a fixed support,
   a piston-cylinder actuator carried by said support and comprising a piston,
   a source of an inhalable gas under superatmospheric pressure,
   a reservoir which is adapted to expand in response to its internal pressure,
   a respiration mask adapted to be applied to the face of the patient,
   an inlet valve connected between said source and said actuator and adapted to admit inhalable gas from said source to said actuator on one side of said piston,
   an outlet valve connected between said actuator and said reservoir and adapted to release inhalable gas from said actuator on said one side of said piston into said reservoir,
   a conduit which incorporates a shut-off valve and which connects said reservoir to said respiration mask,
   first spring means opposing a movement of said piston under the influence of said inhalable gas admitted to said actuator from said source,
   second spring means opposing the expansion of said reservoir,
   ram means adjustably mounted relative to said fixed support structure for engagement with the chest of said patient and which is connected to said piston to be forced against the chest of said patient by the movement of said piston under the influence of said inhalable gas admitted to said actuator from said source,
   stop means arranged to limit the movement of said piston under the influence of said inhalable gas admitted to said actuator from said source, and
   adjusting means for simultaneously adjusting said stop means in direct response to the adjustment of said ram relative to said support into engagement with said chest, whereby said stop is moved to a position in which said stop limits said movement of said piston to an extent that depends on the diameter of said chest.

2. An appliance as set forth in claim 1, in which said stop means comprises a wedge which is adjustable by said adjusting means transversely to the direction of said movement of said piston.

3. An appliance as set forth in claim 2, in which
   said actuator is carried by a vertically adjustable arm,
   said ram means is directly connected to said actuator,
   said support comprises a vertical guide in guiding engagement with said arm,
   a rope is connected between said wedge and said guide, and
   third spring means are provided which act on said wedge in a sense to tension said rope.

4. An appliance as set forth in claim 3, in which said rope is trained around a reversing pulley rotatably mounted in said arm.

5. An appliance as set forth in claim 2, in which said ram has a slot and said wedge extends into said slot.

6. An appliance as set forth in claim 1, in which
   said actuator is fixed to said support,
   said ram means is connected to said actuator by a first lever connected to said actuator, a second lever connected to said ram means, a horizontal pivot pivotally connecting said levers, and means for non-rotatably connecting said levers in different angular positions relative to each other, and
   said adjusting means is connected between said second lever and said stop.

7. An appliance as set forth in claim 6, in which said adjusting means is adapted to adjust said stop to a position which permits said piston to perform a largest movement under the influence of said inhalable gas admitted thereto from said source and has a backlash which is equal to the pivotal movement imparted to said second lever by said piston as a result of said largest movement thereof.

* * * * *